US00PP20022P2

(12) United States Plant Patent
Dekker

(10) Patent No.: US PP20,022 P2
(45) Date of Patent: May 26, 2009

(54) ***CHRYSANTHEMUM* PLANT NAMED 'DEKALLPURE'**

(50) Latin Name: *Chrysanthemum×morifolium*
Varietal Denomination: Dekallpure

(75) Inventor: Cornelis W. Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 0 days.

(21) Appl. No.: 12/156,712

(22) Filed: Jun. 3, 2008

(51) Int. Cl.
*A01H 5/00* (2006.01)

(52) U.S. Cl. ..... Plt./297
(58) Field of Classification Search ..... Plt./297
See application file for complete search history.

*Primary Examiner*—Kent L Bell
(74) *Attorney, Agent, or Firm*—C. A. Whealy

(57) ABSTRACT

A new and distinct cultivar of *Chrysanthemum* plant named 'Dekallpure', characterized by its large semi-double-type inflorescences with soft pink-colored ray florets; strong and upright flowering stems; freely flowering habit; early and uniform flowering response; and good postproduction longevity.

2 Drawing Sheets

Botanical designation: *Chrysanthemum×morifolium.*
Cultivar denomination: 'Dekallpure'.

BACKGROUND OF THE INVENTION

The present invention relates to a new and distinct cultivar of *Chrysanthemum* plant, botanically known as *Chrysanthemum×morifolium,* commercially grown as a cut flower and hereinafter referred to by the name 'Dekallpure'.

The new *Chrysanthemum* is a product of a planned breeding program conducted by the Inventor in Hensbroek, The Netherlands. The objective of the breeding program is to create new freely flowering semi-double-type *Chrysanthemum* cultivars with unique ray floret coloration and excellent postproduction longevity.

The new *Chrysanthemum* originated from a cross-pollination made by the Inventor in Hensbroek, The Netherlands on Mar. 24, 2006 of a proprietary selection of *Chrysanthemum×morifolium* identified as code number 46965, not patented, as the female, or seed, parent with a proprietary selection of *Chrysanthemum×morifolium* identified as code number 04.41785.04, not patented. The new *Chrysanthemum* was discovered and selected by the Inventor as a flowering plant from within the progeny of the stated cross-pollination in a controlled greenhouse environment in Hensbroek, The Netherlands on Oct. 20, 2006.

Asexual reproduction of the new *Chrysanthemum* by terminal cuttings in a controlled greenhouse environment in Hensbroek, The Netherlands since Nov. 5, 2006, has shown that the unique features of this new *Chrysanthemum* are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dekallpure'. These characteristics in combination distinguish 'Dekallpure' as a new and distinct cultivar of *Chrysanthemum:*

1. Large semi-double-type inflorescences with soft pink-colored ray florets.
2. Strong and upright flowering stems.
3. Freely flowering habit.
4. Early and uniform flowering response; plants flower about 36 days after the start of photoinductive treatments.
5. Good postproduction longevity; plants maintain good substance for about three weeks in an interior environment.

Plants of the new *Chrysanthemum* differ from plants of the female parent selection in the following characteristics:

1. Plants of the new *Chrysanthemum* are more vigorous than plants of the female parent selection.
2. Plants of the new *Chrysanthemum* are more freely flowering than plants of the female parent selection.
3. Plants of the new *Chrysanthemum* and the female parent selection differ in ray floret color as plants of the female parent selection have darker pink-colored ray florets.

Plants of the new *Chrysanthemum* differ from plants of the male parent selection in the following characteristics:

1. Plants of the new *Chrysanthemum* have smaller leaves than plants of the male parent selection.
2. Plants of the new *Chrysanthemum* have larger inflorescences than plants of the male parent selection.
3. Plants of the new *Chrysanthemum* flower earlier than plants of the male parent selection.

Plants of the new *Chrysanthemum* can be compared to plants of the *Chrysanthemum×morifolium* 'Oscar', not patented. In side-by-side comparisons conducted in Hensbroek, The Netherlands, plants of the new *Chrysanthemum* differed from plants of 'Oscar' in the following characteristics:

1. Plants of the new *Chrysanthemum* flowered about twelve days earlier than plants of 'Oscar'.

2. Plants of the new *Chrysanthemum* had larger inflorescences than plants of 'Oscar'.
3. Inflorescences of plants of the new *Chrysanthemum* had larger disc diameters than inflorescences of plants of 'Oscar'.
4. Plants of the new *Chrysanthemum* had lighter pink-colored ray florets than plants of 'Oscar'.

BRIEF DESCRIPTION OF THE PHOTOGRAPHS

The accompanying colored photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph on the first sheet comprises a side perspective view of a typical flowering stem of 'Dekallpure' grown as a spray type.

The photograph on the second sheet comprises close-up views of the upper and lower surfaces of typical inflorescences and leaves of 'Dekallpure'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown during the winter and early spring in Hensbroek, The Netherlands, under commercial practice in a glass-covered greenhouse. Plants were initially given two weeks of long day/short night treatments followed by short day/long night treatments to induce flower initiation and development. During the production of the plants, day temperatures ranged from 18° C. to 25° C., night temperatures ranged from 20° C. to 22° C. and light levels were about 7 kilolux. Plants were pinched one time and were 7.5 weeks from planting when the photographs and the description were taken.

Botanical classification:

*Chrysanthemum×morifolium* 'Dekallpure'.

Parentage:

*Female, or seed, parent.*—Proprietary selection of *Chrysanthemum×morifolium* identified as code number 46965, not patented.

*Male, or pollen, parent.*—Proprietary selection of *Chrysanthemum×morifolium* identified as code number 04.41785.04, not patented.

Propagation:

*Type.*—Terminal vegetative cuttings.

*Time to initiate roots.*—About four to six days at 20° C.

*Time to produce a rooted young plant.*—About 13 to 15 days at 20° C.

*Root description.*—Fine, fibrous; light brown in color.

*Rooting habit.*—Freely branching, moderately dense.

Plant description:

*Appearance/growth habit.*—Herbaceous semi-double-type cut flower that is typically grown as a spray-type. Moderately vigorous growth habit.

*Flowering stem description.*—Aspect: Erect. Length: About 60 cm. Spray diameter: About 10 cm to 15 cm. Diameter: About 5 mm. Lateral branch length: About 14 cm to 16 cm. Internode length: About 1.5 cm. Texture: Finely pubescent; longitudinally ridged. Color: Close to 146A.

*Foliage description.*—Arrangement: Alternate; simple. Length: About 5 cm to 10 cm. Width: About 3.5 cm to 4.5 cm. Apex: Cuspidate. Base: Attenuate. Margin: Palmately lobed; sinuses parallel to divergent. Texture, upper and lower surfaces: Pubescent, slightly rough; veins prominent on lower surface. Venation pattern: Pinnate, reticulate. Color: Developing foliage, upper surface: Close to 137C. Developing foliage, lower surface: Lighter than 147B. Fully expanded foliage, upper surface: Close to 147A; venation, close to 146A. Fully expanded foliage, lower surface: More green than 147B; venation, 146B. Petiole: Length: About 1 cm to 2.5 cm. Diameter: About 2 mm to 3 mm. Texture, upper and lower surfaces: Slightly rough. Color, upper and lower surfaces: Close to 146C.

Inflorescence description:

*Appearance.*—Semi-double-type inflorescence form with obovate to oval-shaped ray florets. Inflorescences borne on terminals, arising from leaf axils. Ray and disc florets develop acropetally on a capitulum. Inflorescences slightly fragrant.

*Flowering response.*—Under natural conditions, plant flower in the autumn/winter in the Northern Hemisphere. At other times of the year, inflorescence initiation and development can be induced under short day/long night conditions (at least 13.5 hours of darkness). Early and uniform flowering response; plants exposed to two weeks of long day/short night conditions after planting followed by photoinductive short day/long night conditions flower about 36 days later when grown as a spray-type.

*Postproduction longevity.*—In an interior environment, inflorescences and foliage will maintain good color and substance for about three weeks. Inflorescences persistent.

*Quantity of inflorescences.*—Freely flowering habit; when grown as a spray type, about 15 to 20 inflorescences per flowering stem develop.

*Inflorescence size.*—Diameter: About 4 cm. Depth (height): About 1.5 cm. Disc diameter: About 1 cm. Receptacle height: About 5 mm. Receptacle diameter: About 7 mm. Receptacle color: Close to 145B.

*Inflorescence buds.*—Shape: Flattened spherical. Height: About 3 mm. Diameter: About 6 mm to 7 mm. Color: Close to 147A.

*Ray florets.*—Length: About 1.2 cm to 2 cm. Width: About 5 mm to 8 mm. Shape: Obovate to oval. Apex: Emarginate. Base: Attenuate. Margin: Entire. Angle: Initially upright to close to about 45° to 60° from vertical. Texture, upper and lower surfaces: Smooth, glabrous; satiny. Number per inflorescence: About 40 arranged in about three whorls. Color: When opening, upper and lower surfaces: Close to N155B. Fully opened, upper surface: Close to 75C; color becoming closer to 69B with development. Fully opened, lower surface: Close to 75D; color becoming closer to 69C with development.

*Disc florets.*—Shape: Fused tubular, elongated. Apex: Dentate. Length: About 3 mm to 4 mm. Diameter: About 1 mm. Number per inflorescence: About 235, massed at the center. Color, immature: Apex: Close to N144A to N144B. Mid-section: Close to 2B. Base: Close to 150D. Color, mature: Apex: Close to 2A. Mid-section: Close to 145D. Base: Close to 150D.

*Involucral bracts.*—Length: About 8 mm to 9 mm. Width: About 4 mm to 5 mm. Shape: Ovate. Apex: Obtuse. Base: Obtuse to truncate. Margin: Entire. Texture, upper and lower surfaces: Smooth, glabrous. Number per inflorescence: About 50 arranged in about four whorls. Color, upper and lower surfaces: Close to 147A.

*Peduncles.*—Length: About 6 cm to 9 cm. Diameter: About 2 mm to 3 mm. Angle: Erect to about 30° from vertical. Strength: Moderately strong. Texture: Pubescent; longitudinally ridged. Color: Close to 146A to 146B.

*Reproductive organs.*—Androecium: Not observed. Gynoecium: Present on both ray and disc florets. Style length: About 4 mm. Style color: Close to 145D. Stigma color: Close to 2A.

*Seed/fruit.*—Seed and fruit production has not been observed.

Disease/pest resistance: Resistance to pathogens and pests common to *Chrysanthemums* has not been observed on plants grown under commercial conditions.

It is claimed:

1. A new and distinct *Chrysanthemum* plant named 'Dekallpure' as illustrated and described.

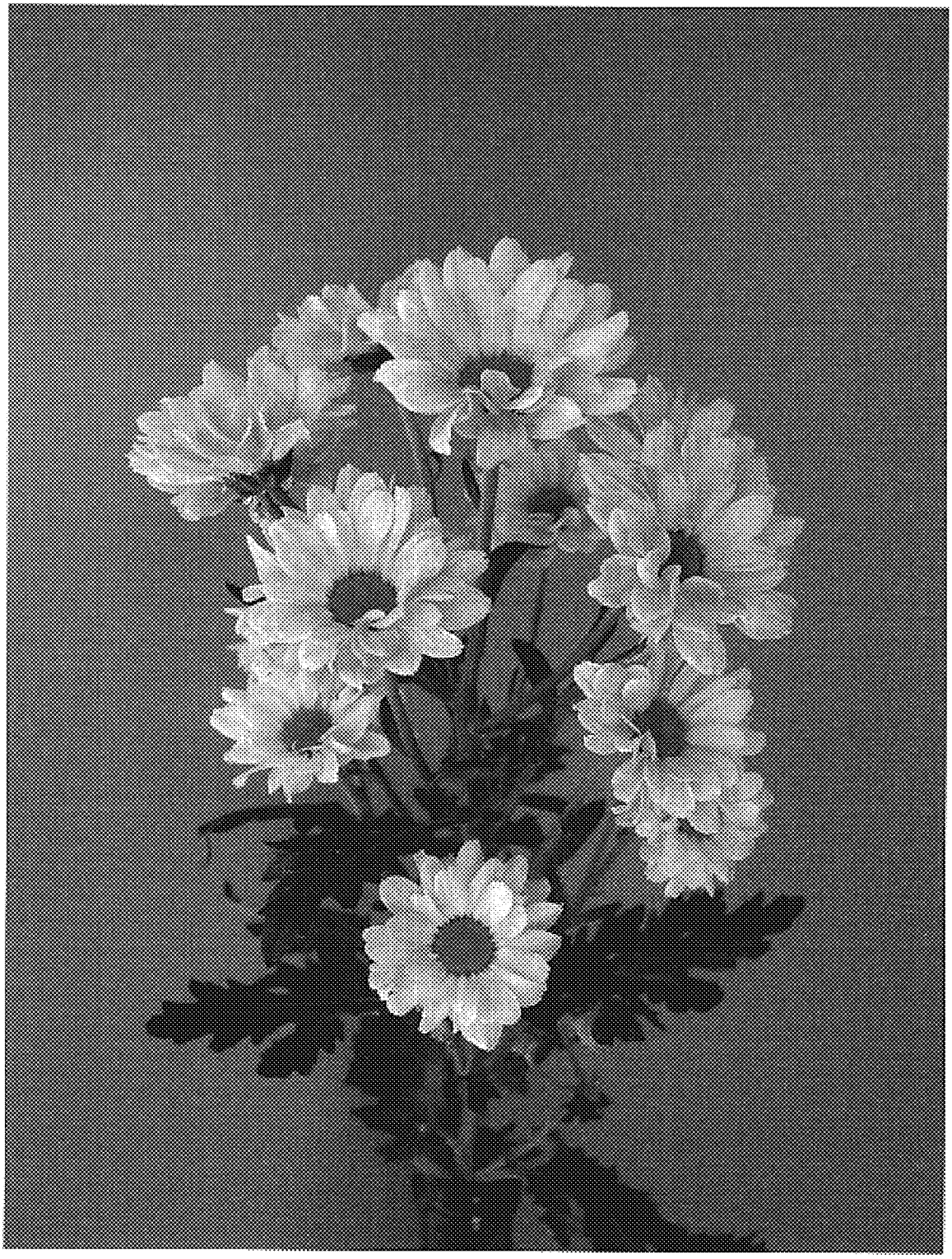

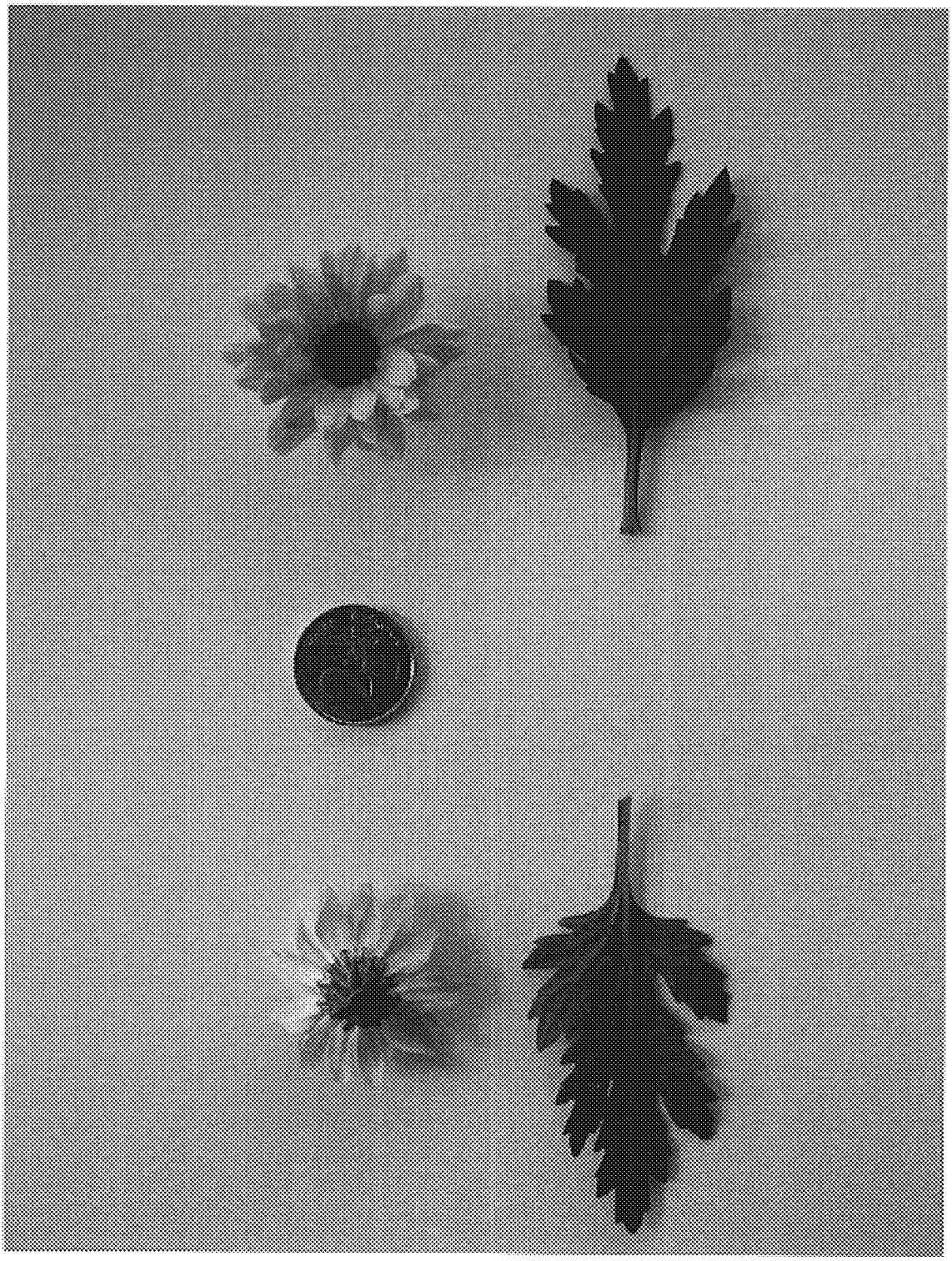

* * * * *